(12) United States Patent
Mahler (10) Patent No.: US 10,234,453 B2
(45) Date of Patent: Mar. 19, 2019

(54) METHOD FOR INCREASING SPECIFICITY OF DIAGNOSTIC TESTS FOR AUTOIMMUNE DISEASES

(75) Inventor: Michael Mahler, Bad Neuenahr (DE)

(73) Assignee: Inova Diagnostics, Inc., San Diego, CA (US)

( * ) Notice: Subject to any disclaimer, the term of this patent is extended or adjusted under 35 U.S.C. 154(b) by 517 days.

(21) Appl. No.: 14/130,429

(22) PCT Filed: Jul. 1, 2011

(86) PCT No.: PCT/US2011/042783
§ 371 (c)(1),
(2), (4) Date: May 16, 2014

(87) PCT Pub. No.: WO2013/006156
PCT Pub. Date: Jan. 10, 2013

(65) Prior Publication Data
US 2014/0363829 A1    Dec. 11, 2014

(51) Int. Cl.
*G01N 33/53* (2006.01)
*G01N 33/564* (2006.01)

(52) U.S. Cl.
CPC ....... *G01N 33/564* (2013.01); *G01N 33/5306* (2013.01); *G01N 2800/10* (2013.01); *G01N 2800/101* (2013.01); *G01N 2800/104* (2013.01)

(58) Field of Classification Search
CPC ......... G01N 2800/10; G01N 2800/101; G01N 2800/104; G01N 33/5306; G01N 33/564
See application file for complete search history.

(56) References Cited

U.S. PATENT DOCUMENTS 6,750,052 B1    6/2004    Shinohara et al.

FOREIGN PATENT DOCUMENTS

| GB | 2426581 A | 11/2006 |
|---|---|---|
| JP | 2004-511805 A | 4/2004 |
| JP | 2004-151000 A | 5/2004 |

OTHER PUBLICATIONS

Dellavance et al. (The Journal of Rheumatology 2005;32:2144-9).*
Ogawa et al., (Journal of autoimmunity 2004, 23, p. 221-231).*
Muro et al (Journal of Autoimmunity 26 (2006) 252e257.*
Ochs et al (J Allergy Clin Immunol. Jun. 2000;105(6 Pt 1):1211-20, Abstract).*
(Colman et al., Res Immunol. Jan. 1994;145(1):33-6).*
Lerner et al., Nature 1982; 299:592-596, see p. 595-596.*
Fritzler ,Arthritis & Rheumatism vol. 63, No. 1, Jan. 2011, pp. 19-22.*
Czernik et al., "Production of phosphorylation state-specific antibodies," Methods Enzymol. 201:264-283 (1991).
Dellavance et al., "The clinical spectrum of antinuclear antibodies associated with the nuclear dense fine speckled immunofluorescence pattern," J. Rheumatol. 32(11):2144-2149 (2005).
Friou, "Fluorescent spot test for anti-nuclear antibodies," Arthritis Rheum. 5:407-410 (1962).
Kumar et al., "Antinuclear antibodies and their detection methods in diagnosis of connective tissue diseases: a journey revisited," Diagn. Pathol. 4:1 (2009).
Mahler et al., "Importance of the dense fine speckled pattern on HEp-2 cells and anti-DFS70 antibodies for the diagnosis of systemic autoimmune diseases," Autoimmun. Rev. 11(9):642-645 (2012) (Epub Nov. 11, 2011).
Merrifield, "Solid Phase Peptide Synthesis. I. The Synthesis of a Tetrapeptide," J. Am. Chem. Soc. 85:2149-2154 (1963).
Ochs et al., "Autoantibodies in interstitial cystitis," J. Urol. 151(3):587-592 (1994).
Ogawa et al., "Autoantigenicity of DFS70 is restricted to the conformational epitope of C-terminal alpha-helical domain," J. Autoimmun. 23(3):221-231 (2004).
Watanabe et al., "Anti-DFS70 antibodies in 597 healthy hospital workers," Arthritis Rheum. 50(3):892-900 (2004).
Yamada et al., "Humoral immune response directed against LEDGF in patients with VKH," Immunol. Lett. 78(3):161-168 (2001).

* cited by examiner

*Primary Examiner* — Julie Wu
*Assistant Examiner* — Carmencita M Belei
(74) *Attorney, Agent, or Firm* — Jones Day (57) ABSTRACT

Provided is a method for increasing the specificity of an antibody-based test to help in the diagnosis of autoimmune diseases by contacting a subject's sample with a blocking antigen prior to testing that is capable of binding to any interfering antibody present in the sample. More specifically, a method for increasing specificity of an antibody-based autoimmune disease assay comprising the steps of providing a sample from a subject, contacting the sample with a DFS70 derived antigen, reacting the sample with an autoimmune disease target and detecting antibodies to the autoimmune disease target is disclosed.

11 Claims, 2 Drawing Sheets
Specification includes a Sequence Listing.

```
  1 MTRDFKPGDL IFAKMKGYPH WPARVDEVPD GAVKPPTNKL PIFFFGTHET AFLGPKDIFP
 61 YSENKEKYGK PNKRKGFNEG LWEIDNNPKV KFSSQQAATK QSNASSDVEV EEKETSVSKE
121 DTDHEEKASN EDVTKAVDIT TPKAARRGRK RKAEKQVETE EAGVTTATA SVNLKVSPKR
181 GRPAATEVKI PKPRGRPKMV KQPCPSESDI ITEEDKSKKK GQEEKQPKKQ PKKDEEGQKE
241 EDKPRKEPDK KEGKKEVESK RKNLAKTGVT STSDSEEEGD DQEGEKKRKG GRNFQTAHRR
301 NMLKGQHEKE AADRKRKQEE QMETEQQNKD EGKKPEVKKV EKKRETSMDS RLQRIHAEIK
361 NSLKIDNLDV NRCIEALDEL ASLQVTMQQA QKHTEMITTL KKIRRFKVSQ VIMEKSTMLY
421 NKFKNMFLVG EGDSVITQVL NKSLAEQRQH EEANKTKDQG KKGPNKKLEK EQTGSKTLNG
481 GSDAQDGNQP QHNGESNEDS KDNHEASTKK KPSSEERETE ISLKDSTLDN
```

METHOD FOR INCREASING SPECIFICITY OF DIAGNOSTIC TESTS FOR AUTOIMMUNE DISEASES

CROSS-REFERENCE TO RELATED APPLICATIONS

This application is a National Stage application under 35 USC § 371 of international application number PCT/US2011/042783, filed Jul. 1, 2011, which is incorporated by reference herein in its entirety.

TECHNICAL FIELD

The present invention relates generally to a method for increasing the specificity of antibody-based tests to help in the diagnosis of autoimmune diseases. More specifically, the present invention relates to a method for increasing the specificity of such a diagnostic test by contacting a subject sample with a blocking antigen prior to testing that is capable of binding to any interfering antibody present in the sample.

BACKGROUND OF THE INVENTION

The detection of antibodies in biological samples to help in the diagnosis of diseases, infection or an immune reaction is known in the art. For some indications, such as autoimmune diseases, these antibodies are autoantibodies that recognize and complex with "self antigens," molecules within a person's own body that are capable of stimulating autoimmunity. Autoimmune disease arises when the body initiates an immune response against its own tissues and organs. When this occurs, the immune system produces antibodies, also known as autoantibodies that target and attack cells or tissues of the body. This reaction is called an autoimmune response and is characterized most commonly by inflammation and tissue damage. Therefore, autoimmune diseases are a major health risk worldwide. The actual number of individuals that suffer from autoimmune disease is not known due to lack of recorded statistics. However, this number is expected to increase dramatically in the next decade because of a number of factors, including increasing environmental pollution. In particular, environmental pollution, such as ultraviolet radiation, ozone, organic solvents and ultrafine particles have been linked to inducing and/or exacerbating autoimmune diseases. Today, there are over eighty illnesses caused by autoimmunity, and several others are believed to be the result of this condition. Approximately 5-7% of all Americans are affected by these diseases and over 75% of those are women. In fact, it is one of the ten leading causes of death in women in all age groups up to 65 years. By comparison, approximately 23.5 million people in the United States suffer from autoimmune disease as compared to 9.0 million that have cancer.

Some autoimmune diseases are tissue- or organ-specific, while others affect several organs of the human body. Diseases of this latter category are often termed "systemic autoimmune rheumaticdiseases ("SARD"), and the symptoms may vary from one patient to the next, with tissue injury and inflammation occurring in multiple sites and organs without relation to their antigenic makeup. Some of the more common SARD include rheumatoid arthritis, systemic lupus erythematosus (lupus), mixed connective tissue disease systemic sclerosis, polymyositis, dermatomyositis, Sjögren's syndrome, and the like. Autoimmune diseases are generally believed to be influenced by multiple factors, with some of the contributing factors being genetic disposition, host factors (such as T cell defects and polyclonal stimulation of B cells that are resistant to controls), environmental factors (such as viruses, chemical agents and certain microbial infections), and antigen-driven mechanisms (such as sequestered antigens or cross-reacting exogenous antigens).

A common characteristic of many SARD is the presence of one or more types of antinuclear antibodies ("ANA") in the bodily fluids of affected patients. Generally, ANAs are autoantibodies directed against antigens in the nucleus of a person's own cells. Thus, various diagnostic ANA assays and screens have been formulated over the years for the detection of ANAs, such as indirect immunofluorescence ("IIF") assays and enzyme linked immunosorbent assays ("ELISAs").

The IIF assay is one of the most commonly used routine tests for the detection of ANAs and is recommended by the American College of Rheumatology ("ACR"). Typically, a patient's serum is diluted in a buffer solution and allowed to react with cells that have been fixed on a glass slide. If there are antibodies in the patient's serum that are immunoreactive with antigen components associated with the cell, they will bind to the cells and form an antigen-antibody complex. After washing to remove any unbound material, the presence of antigen-antibody complexes is detected using an anti-human antibody labeled with a fluorescent moiety. The presence of a fluorescent signal is then detected by viewing the cells under a microscope or more recently with digital imaging systems.

The IIF method is not specific for certain autoimmune diseases because various autoantibody specificities are detected which have different clinical associations. In a significant number of cases, multiple overlapping fluorescent patterns can substantially complicate the interpretation of the pattern. Therefore, specific confirmation tests are mandatory to identify the autoantibody specificities present in the patient's specimen. More specifically, even if a pattern is seen that is suggestive of a specific autoimmune disease, extensive confirmatory testing with purified antigens such as Sm, Scl-70, Ro, La, RNP and double stranded DNA ("dsDNA"), using assays such as enzyme immunoassays ("EIAs"), immunodiffusion or hemagglutination is necessary before one can utilize the test results to help in the diagnosis of the disease. In addition, obscuring of fluorescent patterns can occur, especially if the sample is not titered appropriately. Recent studies have shown that IIF on human epithelial line ("HEp-2") cells has a false positive rate of about 20%. Specifically, when ANA diagnostic tests produce a false positive result, clinicians will typically order a series of confirmatory tests that are both costly and can lead to misdiagnoses. Thus, one of the drawbacks to using the IIF method, for ANA detection, is that it generates a high number of false positives, which can lead to misdiagnosis of patients suffering from an autoimmune disease or conditions that mimic an autoimmune disease, and subsequently unnecessary treatment or insufficient treatment.

Additionally, results can be difficult to interpret and as such, the utilization of specific antibody results is typically less than optimal. Moreover, the delay between the generation of a positive screen and the generation of the specific antibody results can be difficult both for the patient and for the clinician, given the low positive predictive value of the initial result. In particular, when specific antibody results are received, they may be highly suggestive in some eases (e.g., positive anti-Sc1-70 antibody, indicating high likelihood of systemic sclerosis) or they may not be very useful (e.g., positive Ro52 alone, clinical association still unknown). As such, a positive ANA test may yield a sizable portion of ANA-positive individuals with no confirming evidence of autoimmune disease. This becomes even more crucial in view of the perception that autoantibodies may precede the clinical onset of autoimmune disease for many years.

Thus, IIF is a diagnostic method with obvious limitations that does not generate a permanent record, involves multiple assays, is time-consuming, labor intensive and expensive (when personnel and follow-up test costs are considered), requires considerable expertise in the interpretation of results and can lead to misdiagnoses of autoimmune disease.

In recent years, approximately 20% of healthy individuals have been reported to contain ANA, in which anti-dense fine speckles 70 ("anti-DFS70") antibodies represent a major cause of false positive results. Anti-DFS70 antibodies were initially identified as an ANA from a patient with interstitial cystitis, and those autoantibodies were later associated with various other disease conditions such as atopic dermatitis (Ochs et al, 1994 J Urol; 151:587-592). Ochs et al. described the IIF staining pattern by anti-DFS70 antibodies as a characteristic immunohistochemical staining pattern on HEp-2 cells consisting of DFS distributed in the nucleoplasm in interphase cells and with accentuated generalized staining of condensed chromosomes in mitotic cells. Although a 70-kDa protein was recognized by immunoblotting and the antigen was initially termed DFS70, the primary target autoantigen was subsequently identified as the lens epithelium—derived growth factor (LEDGF), also called DNA binding transcription coactivator p75. This protein is believed to have a number of physiological functions, including serving as a cofactor for human immunodeficiency virus replication through an interaction with viral integrase, and it is also highly expressed in prostate tumor tissue.

Since their first characterization, anti-DFS70 antibodies have been found in the sera of patients with a variety of chronic inflammatory conditions, cancer patients, and even frequently in healthy individuals. In 2005, Dellavance et al. (Dellavance et al. 2005 J Rheumatol 32(11):2144-9) evaluated over 10,000 ANA positive samples by HF and then immunoblot, reporting that anti-DFS70 antibodies were common among ANA-positive individuals with no evidence of SARD, and that among autoimmune patients with this autoantibody, over 50% had evidence of autoimmune thyroiditis. The highest prevalence of anti-DFS70 antibodies has been reported in patients with Vogt-Harada syndrome (66.7%) and atopic dermatitis (30%), followed by healthy individuals (~10%), while its prevalence in SARD is significantly lower (~2-3%). Furthermore, when considering the prognostic and long term outcome of individuals who have anti-DFS70 antibodies, it was recently reported that none out of 40 anti-DFS70 positive healthy individuals developed autoimmune disease within an average 4-year interval. Therefore, it has been suggested that anti-DFS antibodies may be utilized as a biomarker to rule out SARD.

However, the potential clinical significance of autoantibodies to DFS70/LEDGF has also been questioned due to conflicting studies. In 2004, Watanabe et al. (Watanabe et al. 2004 Arthritis Rheum 50:892-900) showed that symptoms associated with atopic dermatitis were present among anti-DFS70 positive subjects. Further in contrast, Yamada et al. (Yamada et al. 2001 Immunol Lett 78:161-8) used ELISA to show a high prevalence of autoantibodies to DFS70 in patients with Vogt-Harada syndrome, a systemic autoimmune and inflammatory disorder. Other studies have also demonstrated that autoantibodies to DFS70/LEDGF occur in a variety of chronic inflammatory conditions. Thus, the clinical significance of testing for anti-DFS70 antibodies is still a point of debate as to its association and relevance to diagnosing autoimmune disease. However, a consensus was achieved that anti-DFS70 antibodies are significantly less prevalent in patients with SARD compared to healthy individuals. Therefore, anti-DFS70 antibodies reduce the specificity and thus the positive predictive value of the ANA test.

Accordingly, there is a need in the field for a method that increases the specificity of antibody-based tests for autoimmune diseases that reduces the frequency of false positives in ANA detection, high cost, unnecessary confirmatory testing and misdiagnosis of autoimmune diseases.

BRIEF DESCRIPTION OF THE SEQUENCES

Figure 1:
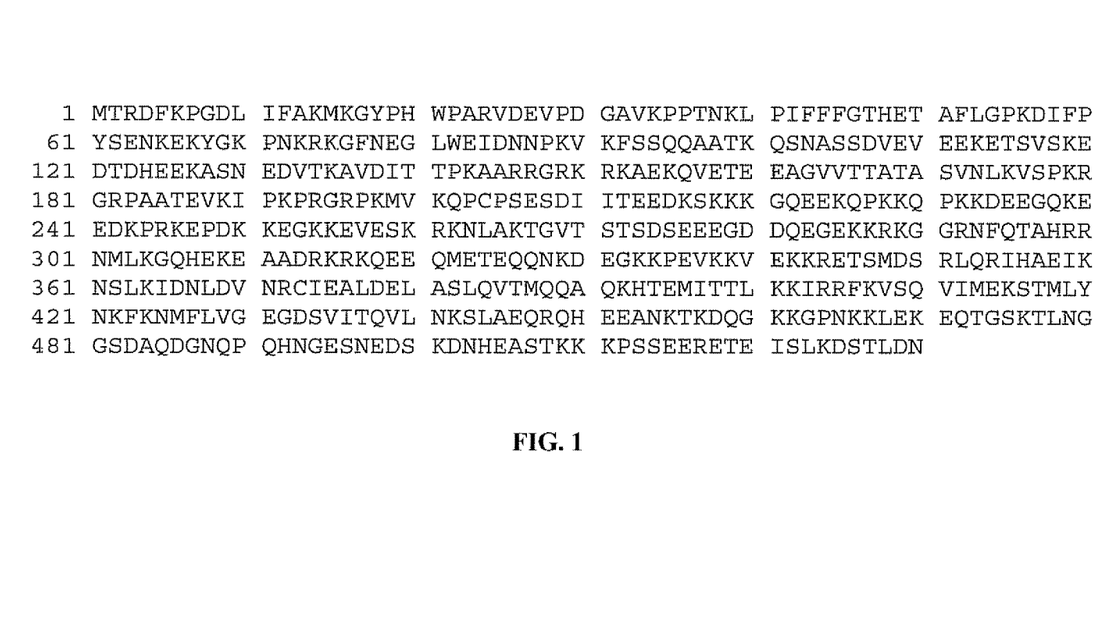
FIG. 1 shows the deduced amino acid sequence of the full-length DFS70 antigen (SEQ ID NO: 1).
Figure 2:
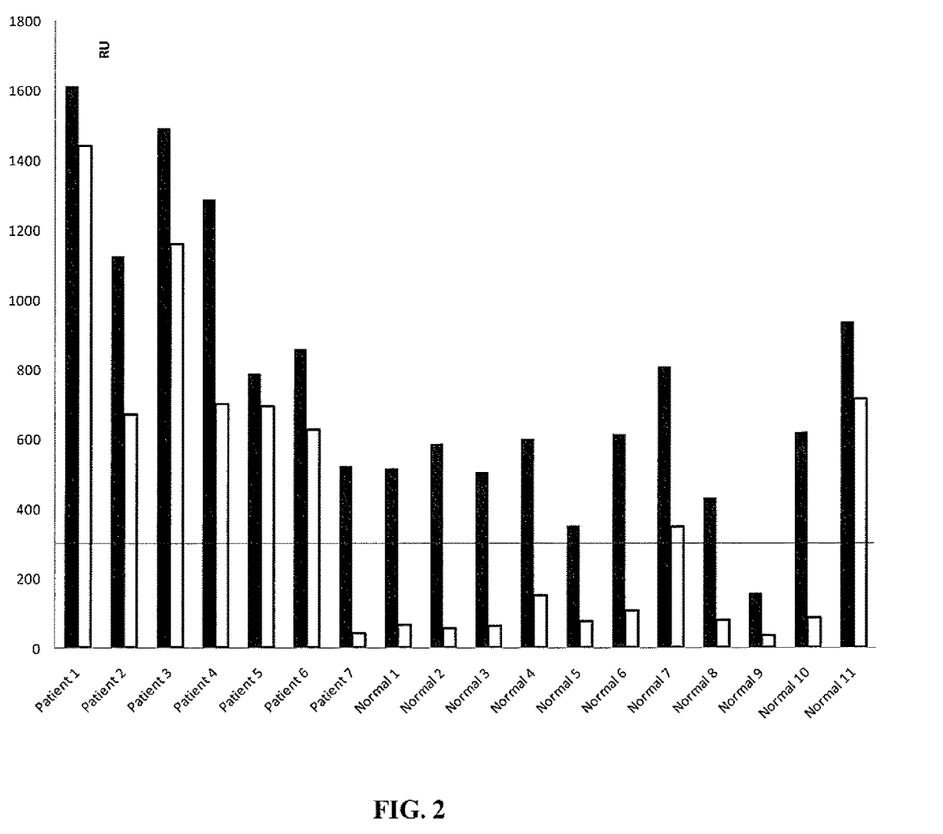
FIG. 2 shows a graph depicting anti-DFS70 reactivity in autoimmune patients and healthy controls both before and after absorption of anti-DFS70 autoantibodies. Before absorption of anti-DFS70 antibodies (black bars), 10/11 of the samples from healthy donors were positive. After absorption (white bars), only 2/10 remained positive.

SEQ ID NO:1 is the amino acid sequence of the full-length DFS70 antigen consisting of 530 amino acids.

SEQ ID NO:2 is the amino acid sequence of a DFS70 derived antigenic fragment corresponding to amino acid residues 1-326 of the full length DFS70 antigen.

SEQ ID NO:3 is the amino acid sequence of a DFS70 derived antigenic fragment corresponding to amino acid residues 323-530 of the full length DFS70 antigen.

SEQ ID NO:4 is the amino acid sequence of a DFS70 derived antigenic fragment corresponding to amino acid residues 375-530 of the full length DFS70 antigen.

SEQ ID NO:5 is the amino acid sequence of a DFS70 derived antigenic fragment corresponding to amino acid residues 323-375 of the full length DFS70 antigen.

SEQ ID NO:6 is the amino acid sequence of a DFS70 derived antigenic fragment corresponding to amino acid residues 323-407 of the full length DFS70 antigen.

SEQ ID NO:7 is the amino acid sequence of a DFS70 derived antigenic fragment corresponding to amino acid residues 349-435 of the full length DFS70 antigen.

SEQ ID NO:8 is the amino acid sequence of a DFS70 derived antigenic fragment corresponding to amino acid residues 349-450 of the full length DFS70 antigen.

SEQ ID NO:9 is the amino acid sequence of a DFS70 derived antigenic fragment corresponding to amino acid residues 349-464 of the full length DFS70 antigen.

SUMMARY OF THE INVENTION

The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one embodiment, the present invention relates to a method for increasing the specificity of an antibody-based autoimmune disease assay comprising the steps of: providing a serum of plasma sample from a patient; contacting the serum or plasma sample with a DFS70 derived antigen to form a complex between the DFS70 derived antigen and anti-DFS70 antibodies that may be present in the sample; reacting the sample with an autoimmune disease target; and detecting antibodies to the autoimmune disease target.

In some exemplary embodiments, the step of contacting the serum or plasma sample with a DFS70 derived antigen to form a complex between the DFS70 derived antigen and anti-DFS70 antibodies that may be present in the sample blocks anti-DFS70 autoantibodies from appearing in the antibody-based autoimmune disease assay results.

In further embodiments of the invention, the step of contacting the serum or plasma sample with a DFS70 derived antigen to form a complex between the DFS70 derived antigen and anti-DFS70 antibodies that may be present in the sample provides for improved identification of other antibodies in the subject sample.

In another embodiment, the present invention relates to a method for increasing the specificity of an antibody-based autoimmune disease assay, wherein the antibody-based autoimmune disease assay is an antinuclear antibody (ANA) test. In other exemplary embodiments, the antibody-based autoimmune disease assay is selected from the group consisting of a fluorescent immunosorbent assay (FIA), a chemiluminescent immunosorbent assay (CIA), a radioimmunoassay (RIA), an enzyme multiplied immunoassay, a solid phase radioimmunoassay (SPRIA) and an enzyme linked immunosorbent assay (ELISA).

In various aspects of the present invention, the DFS70 derived antigen used in the methods as described herein is SEQ ID NO:1. In alternative embodiments, the DFS70 derived antigen comprises an amino acid sequence selected from the group consisting of: SEQ ID NO:2, SEQ ID NO:3, SEQ ID NO:4, SEQ ID NO:5, SEQ ID NO:6; SEQ ID NO:7, SEQ ID NO:8 and SEQ ID NO:9. In other exemplary embodiments, the DFS70 derived antigen is a fragment of the amino acid sequence of DFS70 (SEQ ID NO:1). Additionally, in at least one embodiment of the present invention, the DFS70 derived antigen may be prepared by diluting a DFS70 derived antigen in solution prior to contacting the serum or plasma sample with a DFS70 derived antigen.

In further embodiments of the present invention, the autoimmune disease target is a molecule, or a combination of molecules, associated with a systemic autoimmune disease. In other embodiments, the autoimmune disease target is a molecule, or a combination of molecules, associated with a connective tissue disease. In various aspects of the present invention, the connective tissue disease is selected from the group consisting of, but not limited to: systemic lupus erythematosus (SLE), polymyositis (PM), systemic sclerosis and mixed connective tissue disease (MCTD).

Various exemplary detection methods for detecting antibodies to the autoimmune disease target include using a label selected from the group consisting of a fluorescer, an enzyme, a chemiluminescer, a photosensitizer and suspendable particles.

Other aspects of the invention are found throughout the specification.

DETAILED DESCRIPTION OF THE INVENTION

The present invention relates generally to a method for increasing the specificity of a diagnostic test to help in the diagnosis of autoimmune diseases. More specifically, the present invention relates to a method for increasing the specificity of such a diagnostic test, for example an ANA test, by contacting a subject sample with a specific blocking antigen prior to testing that is capable of binding to interfering autoantibodies present in the sample.

The detection of anti-DFS70 antibodies in subject samples has been shown to produce a significant number of false positives when conducting ANA tests, because certain healthy individuals and individuals with disorders other than SARD have anti-DFS70 antibodies. Furthermore, anti-DFS70 antibodies generate DFS70 fluorescent patterns that obscure immunofluorescence test results, making it harder to identify fluorescent patterns belonging to other detected antibodies. For these reasons, the contribution of anti-DFS70 antibodies to a positive ANA test result can lead to potential misdiagnoses unless extensive confirmatory testing is performed.

Accordingly, the present invention provides a method for increasing the specificity of diagnostic tests to help in the diagnosis of autoimmune diseases, such as ANA tests, wherein pre-incubation with a DFS70 derived antigen allows the DFS70 derived antigen to bind to any anti-DFS70 antibodies present in a subject sample, thereby preventing the detection of anti-DFS70 antibodies. Thus, pre-incubation with a DFS70 derived antigen prevents anti-DFS70 antibodies from being detected, which increases the specificity of an immunodiagnostic test by reducing the number of false positives.

More specifically, the invention provides, in one aspect, a method for increasing the specificity of an ANA test. The method includes: preparing a subject sample from a patient; contacting the subject sample from the subject with a DFS70 derived antigen, or blocking antigen, to bind any interfering anti-DFS70 antibodies that may be present in the subject sample; reacting the subject sample with an autoimmune disease target; and detecting binding of one or more antibodies in the subject sample to an autoimmune disease target in the subject sample. The blocking antigen can be the full length DFS70 antigen (SEQ ID NO: 1) or a fragment thereof that includes an epitope, such as any of the exemplary DFS70 derived antigens exemplified in SEQ ID NOS: 2-9.

As discussed, there are several advantages to using the methods described in the present invention. The occurrence of false positives is reduced significantly, in some cases a reduction of up to 50% of non-disease associated antibodies. Further, another advantage is the unmasking of clinically relevant patterns associated with systemic autoimmune diseases that have been obscured by the DFS70 fluorescent pattern. Specifically, when a blocking antigen, exemplified by any DFS70 derived antigen, is contacted with a subject sample, the blocking antigen binds to any anti-DFS70 autoantibodies present in the subject sample. Because the anti-DFS70 autoantibodies are bound to DFS70 derived antigen, the anti-DFS70 autoantibodies are incapable of subsequently binding to a desired autoimmune disease target. Thus, by using a blocking antigen, the specificity and accuracy of an immunodiagnostic test can be increased significantly according to the methods described herein.

DEFINITIONS

In the description that follows, a number of terms used in the field of molecular biology, immunology and medicine are extensively utilized. In order to provide a clear and consistent understanding of the specification and claims, including the scope to be given such terms, the following non-limiting definitions are provided. All references cited herein are incorporated by reference.

When the terms "one," "a," or "an" are used in this disclosure, they mean "at least one" or "one or more," unless otherwise indicated.

The term "autoimmune disease" refers to a disease or disorder arising from immune reactions directed against an individual's own tissues, organs or manifestation thereof or resulting condition therefrom. As used herein the term "autoimmune disease" includes cancers and other disease states where the antibodies that are directed towards self-tissues are not necessarily involved in the disease condition but are still important in diagnostics. Further, in one embodiment, it refers to a condition that results from, or is aggravated by, the production of autoantibodies by B cells of antibodies that are reactive with normal body tissues and antigens. In other embodiments, the autoimmune disease is one that involves secretion of an autoantibody that is specific for an epitope from a self antigen (e.g. a nuclear antigen).

The term "systemic autoimmune disease" refers to a disease, disorder or a combination of symptoms caused by autoimmune reactions affecting more than one organ. Accordingly, the term "systemic autoimmune disease" includes, but is not limited to, Anti-GBM nephritis (Goodpasture's disease), Granulomatosis with polyangiitis (GPA), microscopic polyangiitis (MPA), systemic lupus erythematosus (SLE), polymyositis (PM) or Celiac disease.

The term "connective tissue disease" refers to a disease, disorder or a combination of symptoms caused by autoimmune reactions affecting the connective tissue of the body. Accordingly, the term "connective tissue disease" includes, but is not limited to, systemic lupus erythematosus (SLE), polymyositis (PM), systemic sclerosis or mixed connective tissue disease (MCTD).

The term "antibody" refers to an immunoglobulin molecule that is capable of binding an epitope or antigenic determinant. The term "antibody" includes whole antibodies and antigen-binding fragments thereof, including single-chain antibodies. Accordingly, the term "antibody" includes human antigen binding antibody and antibody fragments, including, but not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. The antibodies may be from any animal origin such as for example mammals including human, murine, rabbit, goat, guinea pig, camel, horse and the like.

The term "antigen" refers to a molecule that is capable of eliciting an immune response. The term "antigen" includes any molecule that is capable of being bound by an antibody. Additionally, the term "antigen" may refer to a proteinaceous or non-proteinaceous antigen. The antigen may be a whole protein or a portion thereof.

The phrase "amino acid substitution" as used herein refers to the replacement or conversion of an amino acid residue in a sequence with another molecule. The molecule may be a natural or non-natural amino acid, an organic molecule or other chemical moiety. In replacement, one amino acid residue in a sequence being synthesized may be replaced with another amino acid residue or molecule. For example, replacing leucine with isoleucine, which would be a conservative substitution wherein one hydrophobic amino acid residue is replaced with another hydrophobic amino acid residue. In conversion, one amino acid residue in a sequence is converted to another amino acid. For example, glutamine may be converted by deamination to glutamic acid, or arginine converted by deiminase to citrulline.

The term "peptide" as used herein refers to a sequence of two or more amino acid residues joined by peptide bonds. A peptide is distinguished from a native protein because its sequence is generally less than the native protein sequence. The peptide may be isolated from a protein digest or synthetically prepared. The amino acid sequence of the peptide may be identical to the native protein sequence or modified. Modification may be by enzymatic conversion of one or more particular amino acid residues into another amino acid residue. In addition, modification may be effected by replacing, deleting or inserting one or more amino acid residues during peptide synthesis.

The term "autoantibody" refers to an immunoglobulin directed against self-protein, carbohydrate, nucleic acid or other molecule present in the human body. More specifically, the term "autoantibody" refers to an antibody that is capable of binding to a self antigen or fragment thereof.

The term "autoimmune disease target" or "target" refers to a molecule, such as an antigen, against which an autoimmune response can be elicited, wherein an elicited response can be detected using a diagnostic assay. More specifically, as used herein, the term "autoimmune disease target" refers to a protein, such as a proteinaceous antigen, that is used to determine the presence, absence, or amount of an antibody in a sample from a subject. Additionally, the "autoimmune disease target" is an immunogenic molecule that shares at least one epitope with a protein from an antigen involved in autoimmune disease.

The term "antibody-based diagnostic test" or "immunodiagnostic test" refers to a diagnostic test, or assay, for detecting the presence or absence of autoantibodies to defined targets, such as self antigens. More specifically, the term "antibody-based diagnostic test" is an assay in which an antibody specifically binds an antigen to provide for the detection and/or quantitation of the antibody or antigen. An "antibody-based diagnostic test" is characterized by the use of specific binding properties of a particular antibody to isolate, target, and/or quantify the antigen.

The term "blocking antigen" refers to any DFS70 derived antigen used as a blocking antigen.

The term "interfering antibody" refers to any antibody that binds to a blocking antigen.

The term "subject sample" refers to various samples including, but not limited thereto, serum, plasma, cell lysate, milk, saliva, vitrous fluid, lacrimal fluid, tissue homogenate, synovial fluid, cerebrospinal fluid, pleural fluid and tissue homogenate. Samples for detecting circulating autoantibodies include, for example, blood, serum and plasma. In one embodiment, for convenience, the sample is plasma or serum, although saliva has been reported to be a suitable biological sample for measuring the presence of anti-microbial autoantibodies as described herein. The term "subject" or "patient" as used herein refers to a variety of animal species that a sample may be obtained from for the detection of the presence of an autoimmune disease. These include but are not limited to mammals, birds, reptiles and fish. More specifically, the subject is a mammal and most specifically, the mammal is a human. The subject may also be suffering from an infectious disease, cancer, a vaccine response, or some other state wherein measuring the antibody response is useful.

Autoimmune Disease

Autoimmune disease occurs when the immune system malfunctions, interpreting the body's own macromolecules or tissues as foreign and producing autoantibodies or immune cells that target and attack particular macromolecules, cells or tissues of the body. As with a normal immune response against a foreign molecule, the autoimmune response also produces different classes at different stages of an autoimmune disease. Every single human organ system, including the nervous, gastrointestinal, endocrine, circulatory systems, as well as connective tissues and eyes can be affected. Autoimmune diseases include more than 80 widely varied chronic illnesses that affect 5-7% of the population, about two thirds of which are women. As a group they are the least understood diseases. It is suspected that these diseases have genetic pre-disposition, but are triggered by an infection or other triggers.

Examples of autoimmune diseases or disorders include, but are not limited to, Acute Disseminated Encephalomyelitis (ADEM), Acute necrotizing hemorrhagic leukoencephalitis, ddison's disease, Agammaglobulinemia, Alopecia areata, Amyloidosis, Ankylosing spondylitis, Anti-GBM nephritis (Goodpasture's disease), Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis and CREST disease.

Other examples include Essential mixed cryoglobulinemia, Demyelinating neuropathies, Dermatitis herpetiformis, Dennatomyositis, Devic's disease (neuromyelitis optica), Discoid lupus, Dressler's syndrome, Endometriosis, Eosinophilic fasciitis, Erythema nodosum, Evans syndrome, Fibromyalgia, Fibrosing alveolitis, Giant cell arteritis (temporal arteritis), Glomerulonephritis, Granulomatosis with Polyangiitis (GPA) see Wegener's, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type 1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid and Optic neuritis.

Still other examples include Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Romberg syndrome, Parsonnage-Turner syndrome, Pars planitis (peripheral uveitis), *Pemphigus*, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, *Scleroderma*, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA) Autoantibodies The human immune system protects the body against infection by generating antibodies against foreign substances or by producing cytotoxic T cells that have receptors that recognize certain peptides from invading or infected cells. Antibodies, also known as immunoglobulins, abbreviated "Ig," are on the surface of B-cells and in blood or other bodily fluids of vertebrates. They are typically composed of basic structural units—each with two large heavy chains and two small light chains—to form, for example, monomers with one basic unit, dimers with two units or pentamers with five units. There are several different types of antibody heavy chains, and several different kinds of antibodies, which are grouped into different isotypes based on which heavy chain they possess. Five different antibody isotypes are known in mammals, IgM, IgA, IgG, IgD and IgE, which perform different roles, and help direct the appropriate immune response to each different type of foreign molecule they encounter.

Although the general structure of all antibodies is very similar, a small region at the tip of the protein is extremely variable, allowing millions of antibodies with slightly different tip structures to exist. This region is known as the hypervariable region which includes the contact determining region (CDR). Each of these variants can bind to a different target, known as an antigen. This huge diversity of antibodies allows the immune system to recognize an equally wide diversity of antigens. The unique part of the antigen recognized by an antibody is called an epitope. These epitopes bind with their corresponding antibody in a highly specific interaction, called induced fit, that allow antibodies to identify and bind only their unique antigen in the midst of the millions of different molecules that make up an organism. Recognition of an antigen by an antibody tags it for attack by other parts of the immune system. Antibodies can also neutralize targets directly by, for example, binding to a part of a pathogen that it needs to cause an infection.

The large and diverse population of antibodies is generated by random combinations of a set of gene segments that encode different antigen binding sites (or paratopes), followed by random mutations in this area of the antibody gene, which create further diversity. Selection of antibodies with high affinity for the pathogen driving the immune response results in an increased production of reactive antibodies. Antibody genes also re-organize in a process called class switching that changes the base of the heavy chain to another, creating a different isotype of the antibody that retains the antigen specific variable region. Class switching allows a single antibody reactivity to be used by several different parts of the immune system. Production of antibodies is the main function of the humoral immune system.

Each antibody class is structurally adapted for a particular biological activity and functions best at a different site in the body. This is why there are several genes for the constant region of the H chain. Thus, each antibody class/subclass, through its Fc region carries out a particular function. In some cases, antibodies of different classes may be expressed at different stages of an infection or disease even thought they have the same biological activity, e.g. IgM and IgG in fixing complement.

Detecting and identifying autoantibodies in these diseases have yielded valuable information for diagnosis, prognosis and treatment of patients with autoimmune diseases. Currently, despite limitations such as unsuitability to high-volume and high-throughput assay techniques, high cost and high level of false-positives, ANA by IIF is still the most popular diagnostic strategy for screening for autoantibodies in sera and plasma from patients suspected of having systemic autoimmune disease. However, a reliable contribution of autoantibody serology to the diagnosis of autoimmune disease still requires multiple assays to be performed.

Recently, however, autoantibodies that produce a staining pattern referred to as nuclear dense fine speckled have been linked to autoimmune disease as a biomarker for ruling out the diagnosis of autoimmune disease.

DFS70

DFS70 was initially identified as a ~70 kDa protein through immunoblotting experiments using the serum from patients with interstitial cystitis. In recent years, approximately 20% of healthy individuals have been reported to contain ANA, in which anti-dense fine speckles 70 ("anti-DFS70") antibodies represent a major cause of false positive results. Anti-DFS70 were initially identified as an ANA from a patient with interstitial cystitis, but those autoantibodies were later associated with various disease conditions and especially atopic dermatitis. The typical IIF staining pattern has been described as DFS distributed throughout the nucleus and on metaphase chromatin. Further, although a 70-kDa protein was recognized by immunoblotting and the antigen was initially termed dense fine speckles 70 (DFS70), the primary target autoantigen was subsequently identified as the lens epithelium-derived growth factor (LEDGF) or DNA binding transcription coactivator p75. This protein is believed to have a number of physiological functions, including serving as a cofactor for human immunodeficiency virus replication through an interaction with viral integrase, and it is also highly expressed in prostate tumor tissue.

Since their first characterization, anti-DFS70 antibodies have been found in the sera of patients with a variety of chronic inflammatory conditions, cancer patients, and even in certain healthy individuals. In 2005, Dellavance et al. evaluated over 10,000 ANA positive samples by IIF and then immunoblot, reporting that anti-DFS70 antibodies were common among ANA-positive individuals with no evidence of autoimmune rheumatic disease ("ARD"), and that among autoimmune patients with this autoantibody, over 50% had evidence of autoimmune thyroiditis. The highest prevalence of anti-DFS70 antibodies has been reported in patients with Vogt-Harada syndrome (66.7%) and atopic dermatitis (30%), followed by healthy individuals (~10%) while its prevalence in ARD is significant lower (~2-3%). Furthermore, when considering the prognostic and long term outcome of individuals that have anti-DFS70 antibodies, it was recently reported that none out of 40 anti-DFS70 positive healthy individuals developed autoimmune disease within an average 4-year interval. This observation is of high importance since certain autoantibodies have been reported to predict the onset of SARD for many years. Therefore, the present invention involves the realization that utilization of the DFS70 protein as a blocking antigen provides diagnostic value in ruling out potential false positive results and thus makes ANA test results more reliable, thereby increasing the likelihood of correct contribution to the diagnosis.

The following teaching discloses various embodiments of the invention. A skilled artisan will readily recognize that other embodiments can be used. Thus, the particular teachings set forth below are not limiting of the specification and claims in any way.

The blocking antigen of the present invention may be purified from a natural source, recombinantly produced or synthetically prepared. It may be a full length protein, a portion of the full length protein or a peptide comprising one or more antigenic determinants from one or more proteins. The sequence may be identical to the native protein sequence or it may be modified.

In addition, expression vectors may be utilized to prepare antigenic peptides. A DNA segment coding for a peptide can be synthesized by chemical techniques, for example, the phosphotriester method of Matteucci, M. D. et al. (J. Am. Chem. Soc., 103:3185 (1981)). The DNA segment can then be ligated into an expression vector and a host cell transformed with the vector can be used to produce the peptide. See, for example, Current Protocols In Molecular Biology, Ausubel, F. M. et al., eds., John Wiley & Sons, New York, N.Y. and U.S. Pat. Nos. 4,237,224, 4,356,270, 4,468,464, 4,683,195 and 4,889,818.

The antigen can also be prepared using the solid-phase synthetic technique initially described by R. B. Merrifield (J. Am. Chem. Soc., 1963, 85:2149-2154). Other synthesis techniques may be found, for example, in Bodanszky, M. et al., Peptide Synthesis, John Wiley & Sons, 2d Ed., (1976) as well as in other reference works known to those skilled in the art. A summary of synthesis techniques may be found in J. Stuart and J. D. Young, Solid Phase Peptide Synthesis, Pierce Chemical Company, Rockford, 111., 3d Ed., Neurath, H. et al., Eds., p. 104-237, Academic Press, New York, N.Y. (1976). Appropriate protective groups for use in such syntheses will be found in the above texts as well as in J. F. W. McOmie, Protective Groups in Organic Chemistry, Plenum Press, New York, N.Y. (1973).

In general, those synthetic methods comprise the sequential addition of one or more amino acid residues or protected amino acid residues to a growing polypeptide chain. In solid phase synthesis, the protected or derivatized amino acid is attached to an inert solid support through its unprotected carboxyl or amino group. The protecting group of the amino or carboxyl group is then selectively removed and the next similarly protected amino acid residue in the sequence is admixed and reacted under conditions suitable for forming the amide linkage with the residue attached to the solid support. The protecting group of the amino or carboxyl group is then removed from this newly added residue, and the next residue in the sequence is then added, and so forth. After all the desired amino acids have been linked in the proper sequence, any remaining terminal and side group protecting groups are removed sequentially or concurrently. The amino acid sequence is then cleaved from the solid support. To control the disulfide bond formation of a peptide having multiple cysteine residues, different protecting groups may be used that can be removed independently allowing only the desired cysteines to be reactive for disulfide linkage formation (Hargittai, B. and Barany, G., 1999, J. Peptide Res. 54:468-479).

The antigen's amino acid sequence may be modified whether purified from a natural source, recombinantly produced or synthetically prepared. The modified antigen is selected to be a functionally or immunologically equivalent variant of biological variations that occur naturally (e.g., allelic variants, orthologs, splice variants or post-translational variants).

Post-translational modifications that occur during the life of a protein are considered "permissible substitutions" of amino acid residues and can enhance the binding of the antigenic sequence to the autoantibody. While not all post-translational modifications of proteins are known, it is anticipated that one skilled in the art would make permissible substitutions within amino acid sequences to determine if enhanced binding can be achieved once such post-translational modifications for that particular protein are identified. ELISAs can readily determine modified sequences having increased reactivity and/or selectivity for an antibody.

Other modifications within the scope of the present invention provide for certain advantages in the use of the antigen, specifically in its ability to mimic the antigenic site of the protein as well as affinity for the autoantibody of interest. These modifications, referred to as "variants," include any amino acid sequence in which one or more residues have been added or inserted, deleted or substituted with another residue. The term "substituted" includes modifications of an existing amino acid residue by sited directed mutagenesis, random mutagenesis or by chemical treatment, such as by enzymatic modification.

Addition variants include N- or C-terminal fusions and intrasequence insertions of single or multiple amino acids. In one type of addition variant, cysteine residues may be added at the ends of the amino acid sequences or inserted between the amino acid sequences. These cysteine residues may be utilized to form disulfide linkages within the peptide or between two or more peptides. It is well known in the art that cyclic peptides, as well as complexes containing multiple copies of antigenic peptides, provide enhanced binding to their targets as compared to their linear counterparts. The number of conformations that may be formed by the peptide will depend on the number of cysteine residues within the amino acid sequence. Control of intramolecular disulfide linkage formation may be accomplished using protecting groups that may be selectively removed (Hargittai, B. and Barany, G., 1999, J. Peptide Res. 54:468-479). It has also been found that preferential disulfide linkages may be formed by inserting charged amino acid residues adjacent to the cysteine residues. Specifically, when a disulfide bridge is preferred between two specific cysteine residues, oppositely charged amino acid residues may be placed adjacent to these cysteines to promote binding through charge interactions. Correspondingly, where certain cysteine residues are flanked by identically charged amino acids, it is anticipated that disulfide formation will not be favored. Further, intramolecular and intermolecular sulfhydryl bridge formation also may be controlled by pH and antigen concentration.

Deletion variants may be prepared by truncations from the N- or C-termini or by removal of amino acid residues intrasequence. Truncations may be prepared by digesting purified antigenic sequences obtained from protein. Alternatively, the antigenic sequence may be prepared synthetically, or recombinantly having intrasequence deletions or terminal truncations.

Amino acid substitutions within the antigenic sequence may be used to alter the function or chemical characteristics of the antigen. Specifically, amino acid residues may be substituted that affect the structure, charge, hydrophobicity or hydrophilicity of the antigenic sequence. For example, the amino acid proline acts to restrict the conformation of antigenic sequences, which can result in enhanced binding activity for the antibody. ELISA can easily determine enhanced activity of these modified antigenic sequences.

The variants may have from 1 to 3, 5, 10, 15, 20, 25 or 50 amino acid substitutions, insertions, additions and/or deletions. The substitutions may be conservative, non-conservative, or a combination of both. The antigenic sequences of the present invention may also comprise at least 2, 5, 10, 15, 20, 25, 30, 35, 40 or 50 consecutive amino acid residues of a natural protein. In addition, they may be at least 50%, 60%, 70%, 80%, 90% or 95% identical to a natural protein. Furthermore, they may have an immunological activity of over 1%, 10%, 25%, 50%, 60%, 70%, 80%, 90%, 95% or 100% of a natural protein.

The blocking antigen of the present invention functions principally to bind to anti-DFS70 autoantibodies in a patient sample such that any anti-DFS70 autoantibodies that may be present are bound and thus cannot participate in a subsequent reaction with an autoimmune disease target. This may be achieved by including a pre-incubation step prior to conducting an immunodiagnostic test of a subject sample with an autoimmune disease target.

For the purposes of the present invention, DFS70 derived antigen used as a blocking antigen may be a naturally occurring DFS70 protein that has been extracted using protein extraction techniques well known to those of skill in the art. Alternatively, in various embodiments, the DFS70 protein or antigen may be a synthetic peptide. In other embodiments, the DFS70 protein may be a recombinant peptide produced through molecular engineering techniques.

In more specific embodiments, the DFS70 blocking antigen of the present invention may be DFS70 derived antigens, wherein the blocking antigen is comprised of at least one fragment of the DFS70 protein. Evidence of varying epitope reactivities in DFS70 derived antigens have been reported by Ogawa et al. (Ogawa et al. 2004 J Autoimmun 23: 221-231) wherein DFS70 constructs comprising different recombinant portions of the DFS70 protein were tested for autoantigenicity. In various embodiments, the DFS70 blocking antigen may be a full length protein or an immunogenic peptide derived from DFS70. Peptide antigens suitable for binding to anti-DFS70 autoantibodies in a patient sample may be designed, constructed and employed in accordance with well-known techniques. See, e.g., Harlow & Lane Eds., Cold Spring Harbor Laboratory (1988); Czernik, Methods in Enzymology, 201: 264-283 (1991); Merrifield, J. Am. Chem. Soc. 85: 21-49 (1962)). Accordingly, it is contemplated in the present invention that DFS70 protein, and fragments thereof, may be suitable for reacting as a blocking antigen in the methods described herein.

It is contemplated that modifications and changes may be made in preparing a DFS70 blocking antigen and still obtain a functional molecule that encodes a protein with desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence and nevertheless obtain a protein with like properties. It is thus contemplated that various changes may be made in the amino acid sequences of various DFS70 derived antigens without appreciable loss in their biological utility or activity.

Pre-Incubation

Preparing a subject sample: In certain embodiments of the invention, a subject sample comprised of sera, plasma or another bodily fluid as previously described is obtained from the subject for pre-incubation with the blocking antigen. Moreover, the subject sample can be in various forms including, but not limited to, liquid, frozen, chilled, lyophilized and other forms as known in the art. The sample may also be subjected to additional purification or treatment steps prior to and/or following the pre-incubation step herein.

In various embodiments that are described below, the use of the term "DFS solution" is to be understood to include DFS70 antigen and DFS70 derived antigen as described above. In an exemplary embodiment, the DFS70 solution may be prepared by diluting DFS70 antigen or DFS70 derived antigen in a buffer to form a DFS70 solution. In other embodiments of the invention, the DFS70 derived antigen may be prepared in various forms including, but not limited to, liquid, frozen, chilled, lyophilized, immobilized on a solid phase by absorption or covalently attached and other forms as known in the art.

Contacting the subject sample with DFS70 derived antigen: An exemplary embodiment of a pre-incubation step involves preparing a DFS70 solution to be used as a diluent, wherein a subject sample is contacted with the DFS70 solution to absorb anti-DFS70 antibodies. In preferable embodiments, the subject sample is contacted with the DFS70 solution under conditions effective and for a period of time sufficient to allow the formation of immune complexes between DFS70 antigen and anti-DFS70 antibodies that may or may not be present in the subject sample.

Unmasking Effect

In various embodiments of the present invention, one of the advantages provided by pre-incubating a subject sample with blocking antigen is an unmasking effect that increases the accuracy of immunodiagnostic tests. In exemplary embodiments, unmasking of other antibodies is achieved when anti-DFS70 antibodies in a patient sample are absorbed by the addition of DFS70 blocking antigen during a pre-incubation step. More specifically, absorption of anti-DFS70 antibodies in the patient sample will prevent the DFS70 pattern from emerging in immunodiagnostic tests with an autoimmune disease target, thereby preventing obscuring the fluorescent patterns belonging to other antibodies. Thus, blocking of the DFS70 pattern from appearing in immunodiagnostic results allows for the improved identification of other autoantibodies associated with systemic autoimmunity. In particular, blocking of DFS70 patterns allows for the identification of autoantibodies that otherwise could not have been achieved, leading to an easier interpretation of the test results and therefore to more accurate diagnoses of autoimmune disease patients.

Assay Format

Useful solid and liquid phase assay methods known in the art may be utilized with the present invention. While one particular assay described herein is an immunofluorescence assay, the present invention is not specifically limited to this type of assay.

Other well known immunoassays that may be adapted to detect the level of autoantibodies in a sample which react with an antigen include enzyme-linked immunosorbent assay (ELISA), fluorescent immunosorbent assay (FIA), chemiluminescent immunosorbent assay (CIA), radioimmuno assay (RIA), enzyme multiplied immunoassay techniques (EMIT), solid phase radioimmunoassay (SPRIA), immunoblotting, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc. Any assay technology that results in a signal imparted by the reaction of autoantibodies with a heterogeneous antigen of this invention is considered in various embodiments of the present invention. Each of those assay methods may employ single or double antibody techniques in which an indicating means is utilized to signal the immunoreaction, and thereby the binding of an autoantibody to be detected with a heterogeneous DFS70 derived antigen of this invention. For a review of the different immunoassays that may be used, see: The Immunoassay Handbook, David Wild, ed., Stockton Press, New York, 1994. A competitive immunoassay with solid phase separation or an immunometric assay for antibody testing is another exemplary assay suitable for use in the present invention. See, The Immunoassay Handbook, chapter 2 and Maggio, Enzyme Immunoassay, CRC Press, Cleveland, Ohio (1981); and in Goldman, Fluorescent Antibody Methods, Academic Press, New York, N.Y. (1980).

For example, one general assay technology determines the presence, and preferably the amount, of autoantibodies in a biological fluid sample in three steps. First, the biological fluid sample is admixed with an antigen to form an immunoreaction admixture. The antigen is preferably operatively linked to a solid support such that the immunoreaction admixture has both a liquid phase and a solid phase. Next the immunoreaction admixture is maintained under biological assay conditions for a time period, typically predetermined, sufficient to form a heterogeneous antigen-autoantibody complex on the solid phase. In heterogeneous assay formats, the reactants are usually separated after the maintenance period, typically by washing and retaining the solid-phase. In the last step the presence and preferably the amount of complex formed in the second step and thereby the presence or amount of autoantibodies in the biological fluid sample is then determined.

The fluorescent antinuclear antibody test (FANA) was designed by George Friou, M.D. in 1957 and is a sensitive screening test used to detect autoantibodies (Friou, G J 1962 Arthritis Rheum 5:407-410). ANAs are found in patients with a variety of autoimmune diseases, such as but not limited to systemic lupus erythematosus, Sjogren syndrome, rheumatoid arthritis, polymyositis, dermatomyositis, systemic sclerosis, Hashimoto thyroiditis, juvenile diabetes mellitus and Addison disease, and pulmonary fibrosis. ANAs can also be found in patients with chronic infections or cancer. Many medications including procainamide, hydralazine, and dilantin can stimulate the production of ANAs. The ANA test is ordered when someone shows signs and symptoms that are associated with SLE or another autoimmune disorder. Those with autoimmune disorders can have a wide variety of symptoms such as low-grade fever, joint pain, fatigue, and/or unexplained rashes that may change over time. In all the above mentioned cases, and further in accordance with the methods and other immunodiagnostic assays described herein, the absorption of anti-DFS70 antibodies significantly improves the accuracy of the FANA.

ANA generate a broad variety of different staining pattern on HEp-2 cells, a cell line which is frequently used for ANA testing. Some patterns are highly indicative for the autoantibody causing the staining pattern (i.e. anti-centromere antibodies) while others are not indicative for a certain antibody specificity. Therefore, extensive confirmation testing is required to identify the antibodies present in the sample.

It is to be understood that the present invention is applicable to a wide variety of screening methods, for which the pre-incubation step described below may be modified suitably accordingly.

EXAMPLES

Example 1

Preparation of Patient Sample

Sera from healthy individuals (n=124, 86 females and 38 males) were obtained from a commercial source (Promedix, Union, N.J.). The average age was 37 years (standard deviation 13.1 years; 17-60 years). Samples from SLE patients were collected at the Faculty of Medicine, Dalhousie University (Halifax, NS, Canada). The diagnosis of the SLE patients was established according to the disease criteria of the ACR. Patient data was anonymously used with consideration of the latest version of the Helsinki Declaration of human research ethics. Collection of patient samples was carried out according to local ethics committee regulations and where required written approval was obtained from the respective Institutional Review Board.

Example 2

Pre-Incubation with Blocking Antigen

The DNA sequence encoding for the recombinant DFS70 antigen fragment was cloned into pIExBac-3 Expression Vector and the recombinant protein was expressed in insect cells (SF9 cells, Invitrogen). Preparation of recombinant DFS70 antigen fragments was based on the methods described in Ogawa et al., (Ogawa et al. 2004 J Autoimmun 23: 221-231), which is incorporated herein by reference. Purification of the his-tagged DFS70 antigen was done using nickel column. Purity of the antigen was verified by gelelectrophoresis and determined to be >95%.

Recombinant DFS70 was diluted in PBS to a final concentration of approximately 0.6 mg/mL. The resulting DFS70 solution was then used as the sample diluent to absorb the anti-DFS70 antibodies. Sera from patients with systemic autoimmune diseases and from healthy individuals which have been previously identified as anti-DFS70 antibody positive (by QUANTA FLASH (chemiluminescent immunoassays (CIA)) DFS70) were diluted 1/40 in a.) PBS and b.) in DFS70 solution. The diluted samples were then tested for ANAs on HEp-2 cells (NOVA LITE (indirect immunofluorescent assays (IFA)), INOVA Diagnostics, San Diego, CA) according to the manufacturer's instruction. Diluted samples were applied to the slides and incubated for 30 minutes. Unbound antibodies were removed by washing. Secondary fluoroscein isothiocyanate (FITC) conjugated antibody was added. The intensity of the fluorescence was then measured using a digital imaging system (NOVA VIEW (automated digital IFA microscope), INOVA Diagnostics, San Diego, CA).

Example 3

Immunodiagnostic Test

Indirect immunofluorescence was done using NOVA LITE®(IFA) HEp-2 cells (INOVA Diagnostics, San Diego, CA). The sera were tested at 1:40 dilution according to the manufacturer's instruction. Reading of the slides was carried out using a IIF digital image system (NOVA VIEW (automated digital IFA microscope), Inova Diagnostics, San Diego, CA).

The QUANTA FLASH[198] (CIA) DFS70 assay is a novel chemiluminescence assay (CIA) performed on the BIO-FLASH® instrument (automated chemiluminescent analyzer, biokit s.a., Barcelona, Spain). The assay uses recombinant DFS70 as previously described, is also currently used for research purposes only and utilizes the BIO-FLASH® instrument (automated chemiluminescent analyzer), containing a luminometer, as well as all the hardware and liquid handling accessories necessary to perform the assay.

A QUANTA FLASH (CIA) type assay was developed using recombinant DFS70 coated onto paramagnetic latex beads. Prior to use, the reagent pack containing all the necessary assay reagents is gently inverted thirty times. The sealed reagent tubes are then pierced with the reagent pack lid. A patient serum sample is prediluted with the BIO-FLASH® sample buffer in a small disposable plastic cuvette. Small amounts of the diluted patient serum, the beads, and the assay buffer are all combined into a second cuvette, mixed, and then incubated for 9.5 minutes at 37 ° C. The magnetized beads are sedimented and washed several times followed by addition of isoluminol conjugated anti-human, IgG and again incubated 9.5 minutes at 37 ° C. The magnetized beads are sedimented and washed repeatedly. The isoluminol conjugate is oxidized when sodium hydroxide solution and peroxide solutions ("Triggers") are added to the cuvette, and the flash of light produced from this reaction is measured as Relative Light Units (RLUs) by the BIO-FLASH® optical system. The RLUs are proportional to the amount of isoluminol conjugate that is bound to the human IgG, which is in turn proportional to the amount of anti-DFS70 antibodies bound to the antigen on the beads.

Antibodies to dsDNA, Chromatin, SS-A (both Ro52 and Ro60), SS-B, Ribosome P, C1Q, RNP and Sm were determined by the QUANTA LITE (enzyme-linked immunosorbent assay (ELISA)) (INOVA, San Diego, US) all performed according to the manufacturer's instructions.

Example 4

Analysis of Results

The data was statistically evaluated using the Analyse-it software (Version 2.03; Analyse-it Software, Ltd., Leeds, UK). The Spearman test was carried out to analyze the correlation between QUANTA Flash DFS70 and IIF with NOVA View. p values <0.05 were considered as significant.

In a cohort of 251 SLE patients, anti-DFS70 antibodies were identified in 7 (2.8%) of the patients. Only 1 out of 7 patients had no other detectable antibodies. In addition, anti-DFS70 antibodies were found in 11 out of 124 (8.9%) apparently healthy individuals.

Ten QUANTA Flash DFS70 positive samples, together with one borderline sample were tested by IIF. All ten positive samples were found to be positive and the borderline sample was negative. 7 of 7 anti-DFS70 positive samples from SLE patients were also positive by IIF.

Only 1 of 7 anti-DFS70 positive SLE (14.3%) patients (or 1/251 SLE, 0.4%) turned negative when the sample dilution was preincubated with DFS70 antigen. In contrast, 8 of 10 (80.0%) apparently healthy individuals turned negative when the sample dilution was preincubated with DFS70 antigen. The two samples that remained positive had at least one additional antibody.

The decrease in reactivity was significantly more pronounced in healthy individuals compared to SLE patients. After immunoabsorption, the average reactivity was 24.5% in healthy individuals and 64.3% in SLE patients compared to the results before absorption.

\* \* \*

The examples set forth above are provided to give those of ordinary skill in the art with a complete disclosure and description of how to make and use the preferred embodiments of the compositions, and are not intended to limit the scope of what the inventors regard as their invention. Modifications of the above-described modes (for carrying out the invention that are obvious to persons of skill in the art) are intended to be within the scope of the following claims. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. All publications, patents, and patent applications cited in this specification are incorporated herein by reference as if each such publication, patent or patent application were specifically and individually indicated to be incorporated herein by reference.

---

What is claimed is:

1. A method for reducing occurrence of false positives of an antibody-based autoimmune disease assay comprising the steps of:
   a. providing a serum or plasma sample from a subject;
   b. preincubating the serum or plasma sample with a dense fine speckles 70(DFS70) derived antigen to form a complex between the DFS70 derived antigen and anti-DFS70 antibodies that may be present in the sample;
   c. reacting the preincubated serum or preincubated plasma sample of step (b) with an autoimmune disease target; and
   d. detecting antibodies to the autoimmune disease target;
   wherein said autoimmune disease target is a molecule associated with systemic autoimmune rheumatic disease or connective tissue disorder;
   wherein the antibody-based autoimmune disease assay is an antinuclear antibody (ANA) test; and
   wherein said DFS70 derived antigen comprise (a) the amino acid sequence of SEQ ID NO: 1, or (b) an antigenic fragment comprising an amino acid sequence selected from the group consisting of SEQ ID NO: 3, SEQ ID NO:7, SEQ ID NO:8 and SEQ ID NO:9.

2. The method according to claim 1, wherein the antibody-based autoimmune disease assay is selected from the group consisting of a fluorescent immunosorbent assay (FIA), a chemiluminescent immunosorbent assay (CLIA), a radioimmunoassay (RIA), an enzyme multiplied immunoassay, a solid phase radioimmunoassay (SPRIA), an indirect immunofluorescence assay (IIF) and an enzyme linked immunosorbent assay (ELISA).

3. The method according to claim 1, wherein the DFS70 derived antigen is prepared by diluting a DFS70 derived antigen in solution prior to step b.

4. The method according to claim 1, wherein the autoimmune disease target is a molecule associated with a systemic autoimmune rheumatic disease.

5. The method according to claim 1, wherein the autoimmune disease target is a molecule associated with a connective tissue disease.

6. The method according to claim 5, wherein the connective tissue disease is selected from the group consisting of: systemic lupus erythematosus (SLE), polymyositis (PM), systemic sclerosis and mixed connective tissue disease (MCTD).

7. The method according to claim 1, wherein detecting antibodies to the autoimmune disease target is by using a label selected from the group consisting of a fluorescer, an enzyme, a chemiluminescer, a photosensitizer and suspendable particles.

8. The method according to claim 1, wherein the DFS70 derived antigen is purified from a natural source, recombinantly produced or synthetically prepared.

9. A method for reducing occurrence of false positives of an antibody-based autoimmune disease assay comprising the steps of:

a. providing a serum or plasma sample from a subject;
b. preincubating the serum or plasma sample with a dense fine speckles 70(DFS70) derived antigen to form a complex between the DFS70 derived antigen and anti-DFS70 antibodies that may be present in the sample;
c. reacting the preincubated serum or preincubated plasma sample of step (b) with an autoimmune disease target; and
d. detecting antibodies to the autoimmune disease target;
whereby said autoimmune disease assay does not detect anti-DFS70 antibodies and the occurrence of false positives of said assay autoimmune disease assay is reduced; and wherein said autoimmune disease target is a molecule associated with systemic autoimmune rheumatic disease or connective tissue disorder;
wherein the antibody-based autoimmune disease assay is an antinuclear antibody (ANA) test; and
wherein said DFS70 derived antigen comprise (a) the amino acid sequence of SEQ ID NO: 1, or (b) an antigenic fragment comprising an amino acid sequence selected from the group consisting of SEQ ID NO:3, SEQ ID NO:7, SEQ ID NO:8 and SEQ ID NO:9.

10. The method according to claim 9, wherein the antibody-based autoimmune disease assay is selected from the group consisting of a fluorescent immunosorbent assay (FIA), a chemiluminescent immunosorbent assay (CLIA), a radioimmunoassay (RIA), an enzyme multiplied immunoassay, a solid phase radioimmunoassay (SPRIA), an indirect immunofluorescence assay (IIF) and an enzyme linked immunosorbent assay (ELISA).

11. The method according to claim 9, wherein the DFS70 derived antigen is prepared by diluting a DFS70 derived antigen in solution prior to step b.

* * * * *

SEQUENCE LISTING

```
<160> NUMBER OF SEQ ID NOS: 9

<210> SEQ ID NO 1
<211> LENGTH: 530
<212> TYPE: PRT
<213> ORGANISM: Artificial Sequence
<220> FEATURE:
<223> OTHER INFORMATION: Synthetic

<400> SEQUENCE: 1

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
                20                  25                  30

Val Lys Pro Pro Thr Asn Lys Leu Pro Ile Phe Phe Phe Gly Thr His
            35                  40                  45

Glu Thr Ala Phe Leu Gly Pro Lys Asp Ile Phe Pro Tyr Ser Glu Asn
        50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
                100                 105                 110

Lys Glu Thr Ser Val Ser Lys Glu Asp Thr Asp His Glu Glu Lys Ala
            115                 120                 125

Ser Asn Glu Asp Val Thr Lys Ala Val Asp Ile Thr Thr Pro Lys Ala
130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205

Asp Ile Ile Thr Glu Glu Asp Lys Ser Lys Lys Gly Gln Glu Glu
    210                 215                 220

Lys Gln Pro Lys Lys Gln Pro Lys Lys Asp Glu Glu Gly Gln Lys Glu
225                 230                 235                 240

Glu Asp Lys Pro Arg Lys Glu Pro Asp Lys Lys Glu Gly Lys Lys Glu
                245                 250                 255
```

```
Val Glu Ser Lys Arg Lys Asn Leu Ala Lys Thr Gly Val Thr Ser Thr
            260                 265                 270

Ser Asp Ser Glu Glu Gly Asp Gln Gly Glu Lys Lys Arg
        275                 280                 285

Lys Gly Gly Arg Asn Phe Gln Thr Ala His Arg Asn Met Leu Lys
    290                 295                 300

Gly Gln His Glu Lys Glu Ala Ala Asp Arg Lys Arg Lys Gln Glu Glu
305                 310                 315                 320

Gln Met Glu Thr Glu Gln Gln Asn Lys Asp Glu Gly Lys Lys Pro Glu
                325                 330                 335

Val Lys Lys Val Glu Lys Lys Arg Glu Thr Ser Met Asp Ser Arg Leu
            340                 345                 350

Gln Arg Ile His Ala Glu Ile Lys Asn Ser Leu Lys Ile Asp Asn Leu
                355                 360                 365

Asp Val Asn Arg Cys Ile Glu Ala Leu Asp Glu Leu Ala Ser Leu Gln
        370                 375                 380

Val Thr Met Gln Gln Ala Gln Lys His Thr Glu Met Ile Thr Thr Leu
385                 390                 395                 400

Lys Lys Ile Arg Arg Phe Lys Val Ser Gln Val Ile Met Glu Lys Ser
                405                 410                 415

Thr Met Leu Tyr Asn Lys Phe Lys Asn Met Phe Leu Val Gly Glu Gly
            420                 425                 430

Asp Ser Val Ile Thr Gln Val Leu Asn Lys Ser Leu Ala Glu Gln Arg
        435                 440                 445

Gln His Glu Glu Ala Asn Lys Thr Lys Asp Gln Gly Lys Lys Gly Pro
                450                 455                 460

Asn Lys Lys Leu Glu Lys Glu Gln Thr Gly Ser Lys Thr Leu Asn Gly
465                 470                 475                 480

Gly Ser Asp Ala Gln Asp Gly Asn Gln Pro Gln His Asn Gly Glu Ser
                485                 490                 495

Asn Glu Asp Ser Lys Asp Asn His Glu Ala Ser Thr Lys Lys Lys Pro
                500                 505                 510

Ser Ser Glu Glu Arg Glu Thr Glu Ile Ser Leu Lys Asp Ser Thr Leu
            515                 520                 525

Asp Asn
    530

<210> SEQ ID NO 2
<211> LENGTH: 326
<212> TYPE: PRT
<213> ORGANISM: Artificial Sequence
<220> FEATURE:
<223> OTHER INFORMATION: Synthetic

<400> SEQUENCE: 2

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Pro Tyr Ser Glu Asn
    50                  55                  60

Lys Glu Lys Tyr Gly Lys Pro Asn Lys Arg Lys Gly Phe Asn Glu Gly
65                  70                  75                  80
```

```
Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205

Asp Ile Ile Thr Glu Glu Asp Lys Ser Lys Lys Gly Gln Glu Glu
    210                 215                 220

Lys Gln Pro Lys Gln Pro Lys Lys Asp Glu Glu Gly Gln Lys Glu
225                 230                 235                 240

Glu Asp Lys Pro Arg Lys Glu Pro Asp Lys Lys Glu Gly Lys Lys Glu
                245                 250                 255

Val Glu Ser Lys Arg Lys Asn Leu Ala Lys Thr Gly Val Thr Ser Thr
            260                 265                 270

Ser Asp Ser Glu Glu Gly Asp Asp Gln Glu Gly Glu Lys Lys Arg
        275                 280                 285

Lys Gly Gly Arg Asn Phe Gln Thr Ala His Arg Asn Met Leu Lys
    290                 295                 300

Gly Gln His Glu Lys Glu Ala Ala Asp Arg Lys Arg Lys Gln Glu Glu
305                 310                 315                 320

Gln Met Glu Thr Glu Gln
                325
```

<210> SEQ ID NO 3
<211> LENGTH: 208
<212> TYPE: PRT
<213> ORGANISM: Artificial Sequence
<220> FEATURE:
<223> OTHER INFORMATION: Synthetic

<400> SEQUENCE: 3

```
Glu Thr Glu Gln Gln Asn Lys Asp Glu Gly Lys Lys Pro Glu Val Lys
1               5                   10                  15

Lys Val Glu Lys Lys Arg Glu Thr Ser Met Asp Ser Arg Leu Gln Arg
            20                  25                  30

Ile His Ala Glu Ile Lys Asn Ser Leu Lys Ile Asp Asn Leu Asp Val
        35                  40                  45

Asn Arg Cys Ile Glu Ala Leu Asp Glu Leu Ala Ser Leu Gln Val Thr
    50                  55                  60

Met Gln Gln Ala Gln Lys His Thr Glu Met Ile Thr Thr Leu Lys Lys
65                  70                  75                  80

Ile Arg Arg Phe Lys Val Ser Gln Val Ile Met Glu Lys Ser Thr Met
                85                  90                  95

Leu Tyr Asn Lys Phe Lys Asn Met Phe Leu Val Gly Glu Gly Asp Ser
            100                 105                 110
```

Val Ile Thr Gln Val Leu Asn Lys Ser Leu Ala Glu Gln Arg Gln His
         115                 120                 125

Glu Glu Ala Asn Lys Thr Lys Asp Gln Gly Lys Lys Gly Pro Asn Lys
130                 135                 140

Lys Leu Glu Lys Glu Gln Thr Gly Ser Lys Thr Leu Asn Gly Gly Ser
145                 150                 155                 160

Asp Ala Gln Asp Gly Asn Gln Pro Gln His Asn Gly Glu Ser Asn Glu
                165                 170                 175

Asp Ser Lys Asp Asn His Glu Ala Ser Thr Lys Lys Pro Ser Ser
         180                 185                 190

Glu Glu Arg Glu Thr Glu Ile Ser Leu Lys Asp Ser Thr Leu Asp Asn
         195                 200                 205

<210> SEQ ID NO 4
<211> LENGTH: 156
<212> TYPE: PRT
<213> ORGANISM: Artificial Sequence
<220> FEATURE:
<223> OTHER INFORMATION: Synthetic

<400> SEQUENCE: 4

Glu Ala Leu Asp Glu Leu Ala Ser Leu Gln Val Thr Met Gln Gln Ala
1               5                   10                  15

Gln Lys His Thr Glu Met Ile Thr Thr Leu Lys Lys Ile Arg Arg Phe
            20                  25                  30

Lys Val Ser Gln Val Ile Met Glu Lys Ser Thr Met Leu Tyr Asn Lys
         35                  40                  45

Phe Lys Asn Met Phe Leu Val Gly Glu Gly Asp Ser Val Ile Thr Gln
50                  55                  60

Val Leu Asn Lys Ser Leu Ala Glu Gln Arg Gln His Glu Glu Ala Asn
65                  70                  75                  80

Lys Thr Lys Asp Gln Gly Lys Lys Gly Pro Asn Lys Lys Leu Glu Lys
                85                  90                  95

Glu Gln Thr Gly Ser Lys Thr Leu Asn Gly Gly Ser Asp Ala Gln Asp
            100                 105                 110

Gly Asn Gln Pro Gln His Asn Gly Glu Ser Asn Glu Asp Ser Lys Asp
        115                 120                 125

Asn His Glu Ala Ser Thr Lys Lys Pro Ser Ser Glu Glu Arg Glu
         130                 135                 140

Thr Glu Ile Ser Leu Lys Asp Ser Thr Leu Asp Asn
145                 150                 155

<210> SEQ ID NO 5
<211> LENGTH: 53
<212> TYPE: PRT
<213> ORGANISM: Artificial Sequence
<220> FEATURE:
<223> OTHER INFORMATION: Synthetic

<400> SEQUENCE: 5

Glu Thr Glu Gln Gln Asn Lys Asp Glu Gly Lys Lys Pro Glu Val Lys
1               5                   10                  15

Lys Val Glu Lys Lys Arg Glu Thr Ser Met Asp Ser Arg Leu Gln Arg
            20                  25                  30

Ile His Ala Glu Ile Lys Asn Ser Leu Lys Ile Asp Asn Leu Asp Val
         35                  40                  45

Asn Arg Cys Ile Glu

50

<210> SEQ ID NO 6
<211> LENGTH: 85
<212> TYPE: PRT
<213> ORGANISM: Artificial Sequence
<220> FEATURE:
<223> OTHER INFORMATION: Synthetic

<400> SEQUENCE: 6

Glu Thr Glu Gln Gln Asn Lys Asp Glu Gly Lys Lys Pro Glu Val Lys
1               5                   10                  15

Lys Val Glu Lys Lys Arg Glu Thr Ser Met Asp Ser Arg Leu Gln Arg
            20                  25                  30

Ile His Ala Glu Ile Lys Asn Ser Leu Lys Ile Asp Asn Leu Asp Val
        35                  40                  45

Asn Arg Cys Ile Glu Ala Leu Asp Glu Leu Ala Ser Leu Gln Val Thr
    50                  55                  60

Met Gln Gln Ala Gln Lys His Thr Glu Met Ile Thr Thr Leu Lys Lys
65                  70                  75                  80

Ile Arg Arg Phe Lys
                85

<210> SEQ ID NO 7
<211> LENGTH: 87
<212> TYPE: PRT
<213> ORGANISM: Artificial Sequence
<220> FEATURE:
<223> OTHER INFORMATION: Synthetic

<400> SEQUENCE: 7

Asp Ser Arg Leu Gln Arg Ile His Ala Glu Ile Lys Asn Ser Leu Lys
1               5                   10                  15

Ile Asp Asn Leu Asp Val Asn Arg Cys Ile Glu Ala Leu Asp Glu Leu
            20                  25                  30

Ala Ser Leu Gln Val Thr Met Gln Gln Ala Gln Lys His Thr Glu Met
        35                  40                  45

Ile Thr Thr Leu Lys Lys Ile Arg Arg Phe Lys Val Ser Gln Val Ile
    50                  55                  60

Met Glu Lys Ser Thr Met Leu Tyr Asn Lys Phe Lys Asn Met Phe Leu
65                  70                  75                  80

Val Gly Glu Gly Asp Ser Val
                85

<210> SEQ ID NO 8
<211> LENGTH: 102
<212> TYPE: PRT
<213> ORGANISM: Artificial Sequence
<220> FEATURE:
<223> OTHER INFORMATION: Synthetic

<400> SEQUENCE: 8

Asp Ser Arg Leu Gln Arg Ile His Ala Glu Ile Lys Asn Ser Leu Lys
1               5                   10                  15

Ile Asp Asn Leu Asp Val Asn Arg Cys Ile Glu Ala Leu Asp Glu Leu
            20                  25                  30

Ala Ser Leu Gln Val Thr Met Gln Gln Ala Gln Lys His Thr Glu Met
        35                  40                  45

Ile Thr Thr Leu Lys Lys Ile Arg Arg Phe Lys Val Ser Gln Val Ile
    50                  55                  60

```
Met Glu Lys Ser Thr Met Leu Tyr Asn Lys Phe Lys Asn Met Phe Leu
65                  70                  75                  80

Val Gly Glu Gly Asp Ser Val Ile Thr Gln Val Leu Asn Lys Ser Leu
                85                  90                  95

Ala Glu Gln Arg Gln His
            100

<210> SEQ ID NO 9
<211> LENGTH: 116
<212> TYPE: PRT
<213> ORGANISM: Artificial Sequence
<220> FEATURE:
<223> OTHER INFORMATION: Synthetic

<400> SEQUENCE: 9

Asp Ser Arg Leu Gln Arg Ile His Ala Glu Ile Lys Asn Ser Leu Lys
1               5                   10                  15

Ile Asp Asn Leu Asp Val Asn Arg Cys Ile Glu Ala Leu Asp Glu Leu
                20                  25                  30

Ala Ser Leu Gln Val Thr Met Gln Gln Ala Gln Lys His Thr Glu Met
            35                  40                  45

Ile Thr Thr Leu Lys Lys Ile Arg Arg Phe Lys Val Ser Gln Val Ile
        50                  55                  60

Met Glu Lys Ser Thr Met Leu Tyr Asn Lys Phe Lys Asn Met Phe Leu
65                  70                  75                  80

Val Gly Glu Gly Asp Ser Val Ile Thr Gln Val Leu Asn Lys Ser Leu
                85                  90                  95

Ala Glu Gln Arg Gln His Glu Glu Ala Asn Lys Thr Lys Asp Gln Gly
            100                 105                 110

Lys Lys Gly Pro
        115
```